(12) United States Patent
Paris

(10) Patent No.: US 10,646,435 B2
(45) Date of Patent: May 12, 2020

(54) PASTY BIO-ADHESIVE SUSTAINED RELEASE COMPOSITIONS

(71) Applicant: Care & Pharma Perspectives SA, Fribourg (CH)

(72) Inventor: Laurence Paris, Montmarault (FR)

(73) Assignee: CARE & PHARMA PERSPECTIVES SA, Fribourg (CH)

( * ) Notice: Subject to any disclaimer, the term of this patent is extended or adjusted under 35 U.S.C. 154(b) by 0 days.

(21) Appl. No.: 15/136,446

(22) Filed: Apr. 22, 2016

(65) Prior Publication Data

US 2016/0235715 A1 Aug. 18, 2016

Related U.S. Application Data

(63) Continuation-in-part of application No. 11/577,503, filed as application No. PCT/FR2005/050869 on Oct. 19, 2005, now abandoned.

(30) Foreign Application Priority Data

Oct. 20, 2004 (FR) ..................................... 04 11156

(51) Int. Cl.
| | |
|---|---|
| A61K 47/36 | (2006.01) |
| A61K 9/00 | (2006.01) |
| A61K 47/24 | (2006.01) |
| A61K 47/10 | (2017.01) |
| A61K 47/02 | (2006.01) |
| A61K 47/26 | (2006.01) |
| A61K 45/00 | (2006.01) |
| A61K 9/107 | (2006.01) |

(52) U.S. Cl.
CPC ............ *A61K 9/0034* (2013.01); *A61K 9/006* (2013.01); *A61K 9/0043* (2013.01); *A61K 9/0048* (2013.01); *A61K 9/107* (2013.01); *A61K 45/00* (2013.01); *A61K 47/02* (2013.01); *A61K 47/10* (2013.01); *A61K 47/24* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 4,910,225 A | * | 3/1990 | Ogawa ................. | A61K 9/0048 514/561 |
| 5,458,904 A | * | 10/1995 | Zolper .................. | A21D 2/183 426/573 |
| 6,482,397 B1 | * | 11/2002 | Scott ........................ | A61K 8/35 424/401 |
| 2002/0107238 A1 | | 8/2002 | Bandyopadhyay et al. | |
| 2003/0083314 A1 | | 5/2003 | Yiv et al. | |
| 2005/0031547 A1 | * | 2/2005 | Tamarkin ............... | A61K 8/046 424/45 |
| 2008/0274191 A1 | * | 11/2008 | Paris .................... | A61K 9/0014 424/488 |

FOREIGN PATENT DOCUMENTS

| | | | | | |
|---|---|---|---|---|---|
| EP | 1807114 | * | 8/2008 | ............. | A61K 47/36 |
| JP | H05503527 A | | 6/1993 | | |
| JP | 2001501194 A | | 1/2001 | | |
| JP | 2002255852 A | | 9/2002 | | |
| JP | 2002540080 A | | 11/2002 | | |
| JP | 2004510809 A | | 4/2004 | | |
| WO | WO9112808 A1 | | 9/1991 | | |
| WO | WO9811874 A1 | | 3/1998 | | |
| WO | WO-9819663 A1 | * | 5/1998 | ............. | A61K 8/042 |
| WO | WO-0170271 A2 | * | 9/2001 | ............. | A61K 8/365 |
| WO | WO 2006/043005 | * | 4/2006 | ............. | A61K 47/36 |

* cited by examiner

*Primary Examiner* — Brian Gulledge
(74) *Attorney, Agent, or Firm* — Young & Thompson

(57) ABSTRACT

The present invention provides pasty or liquid compositions for applications on mucous membranes of cavities easily reached by hand, having a bio-adhesive prolonged effect or release. The composition includes a polysaccharide matrix agent selected from the group constituting of lambda carrageenan and iota carrageenan. The matrix allows the in situ formation of a matrix film with a reinforced bio-adhesive capacity due to complexation reactions between the polysaccharide matrix agent and the components of the local secretions of the mucous membranes. The compositions can also include a lecithin compound as a reinforcing agent of the intrinsic bio-adhesive properties of the polysaccharide matrix agent. The composition can further include at least one of (a) a hydration medium for the polysaccharide matrix agent, (b) a lecithin co-solvent allowing the dispersion of the micellar lecithin solution in the hydration medium, (c) an additive or additives, and (d) at least one active ingredient.

37 Claims, 3 Drawing Sheets

PASTY BIO-ADHESIVE SUSTAINED RELEASE COMPOSITIONS

CROSS REFERENCE TO RELATED APPLICATION

This application is a continuation-in-part claiming priority to currently pending U.S. patent application Ser. No. 11/577,503 filed on Jul. 24, 2007, with the title BIO-ADHESIVE COMPOSITION WITH PROGRAMMED RELEASE, with is a § 371 National Phase Application of PCT/FR2005/050869, filed Oct. 19, 2005, (the entirety of both of which are herein incorporated by reference) which claimed the priority of French Patent Application 0411156, filed Oct. 20, 2004.

FIELD OF THE INVENTION

The present invention relates to the pharmaceutical, cosmetic and nutraceutical field and more particularly to the pasty bio-adhesive systems with mechanical properties or active ingredient programmed release in the human body.

These pasty bio-adhesive compositions are addressed to be applied on mucous membranes, specifically those which can be easily reached by hand.

Indeed, several cavities constitute the human body and are covered by mucous membranes, but some of them are not easily reached by hand like stomach, lungs, urinary tracts, etc. . . . .

Those easily reached by hand are:
  the oral mucous membrane, which extends from the mouth to the esophagus by passing via the throat. Mouth and throat are cavities specifically easily reached by hand.
  the nasal mucous membrane, which extends from the nose to the rear throat
  the rectal mucous membrane covering the distal part of the large intestine
  the vaginal mucous membrane
  the ocular mucous membrane called the cornea.

Even if all cavities are covered by mucous membranes, those in contact with the air (easily reached by hand) are permanently moistened by a secretion containing a polymucosaccharide, the mucin, having its own specificity depending of the cavity itself.

Indeed polymucosaccharides covering the mouth are different in their composition from the vaginal polymucosaccharides.

Same differences are observed for the mucin covering the nasal cavity or the tears humidifying eyes.

These secretions have two major roles concerning the mucous membrane:
  a role of protection against any external stresses
  and a role as lubricant.

It is thus in the case of lachrymal liquid, saliva, and vaginal secretions.

The mucous membranes are the site of a certain number of diseases or local infections if a dryness of one of these is observed.

Therefore, easily reached by hand, a local treatment can be applied onto these mucous membranes.

BACKGROUND OF THE ART

Today a certain number of pharmaceutical products exist to treat local infections or diseases, such as:
  suckable tablets for the treatments of mouth ulcers, stomatitis, gingivitis, glossitis, etc. . . .
  gels and creams for oral, vaginal, and rectal (hemorrhoids), and ocular treatments. As examples:
    Willmott's application WO 01/70271 protects a mixture of carrageenan and *Sclerotium* gum for skin applications surfactant free, the name of this application being: "ACID STABLE BASE COMPOSITIONS FOR PREPARING SURFACTANTFREETOPICAL COMPOSITIONS". Indeed sometime the surfactant irritate the mucous membranes specifically when these are destroyed.
    the PCT application WO0056366 protects "A pharmaceutical composition adapted for use as a spermicide, the composition comprising a gel-microemulsion comprising an oil-in-water microemulsion and a polymeric hydrogel. The gel microemulsion can be used in a spermicidal method. Also, a gel microemulsion pharmaceutical composition adapted for use as a formulation base for additional therapeutic agents."
    The most important ingredients in the gel are Cremophor® ELO and Phospholipids (Phospholipon®). These two ingredients form a microemulsion incorporated in a lambda carrageenan polymeric gel for a vaginal applications.
  liquids for the nasal route (nasal solutes) and for the ocular route (eye lotions). As examples:
    OGAWA protects through his U.S. Pat. No. 4,910,25 a solution containing benzoylphenylacetic acid and its salts for treating inflammatory disease by topical application. The other ingredients used are just pH adjusters (buffer solutions) to maintain a pH around 6 avoiding eyes irritation.
    The PCT/AU91/0063 protects eye drops containing phospholips and or hyaluronic acid dispersed in a carrier (propylene glycol).
    A physiological salt is added in the purpose to maintain a good isotonicity of the medium.

Unfortunately these products have very short action duration, mechanically or therapeutically speaking, from a therapeutic standpoint because of a perpetual "washing out" of these mucous membranes by the secretions.

Indeed nothing in Willmott's application, no more in Ogawa's application, in the PCT application WO0056366 and in the PCT/AU91/0063, speaks about a prolonged release at the targetted point.

So, repeated local administrations are necessary and in certain cases, are not very pleasant for the patient.

Therefore it appears necessary, for the comfort of the patient, to have systems that make it possible to maintain local action duration more substantial than simple creams, in order to reduce the number of applications per day.

Broadly speaking, any system that makes it possible to prolong the mechanical action (lubricating action for example) or the therapeutic effect of an active ingredient in the organism, is called "prolonged effect or programmed release form".

Today most of the systems having a programmed release, have been developed under solid form.

For the oral route, different kinds of tablets have been developed, called matrix (inert, plastic and oily matrices), which slowly release the active ingredient in the stomach or in the intestine.

In a purpose to obtain a potential better bioavailability, different sustained release microgranules contained in a hard capsule were developed, too. After the opening of the hard capsule, each microgranule slowly releases the active ingredient all along the intestinal tract, like if it was a small matrix.

Among all the patents filed in this field, we can cite inter alia,

The international application WO 03101424 mentioning iota carrageenans and other gum like hydroxypropylmethylcellulose or xanthan for the realization of matrices having prolonged release under solid form. In this application the applicant gives the name of "swelling modified system" or "gelling matrix modified release system" to his matrix. This qualification is due to the fact the gums are going to swell in aqueous medium, and slowly releasing the active contained in the mixture of gums. Sodium docecyl sulfate is added in purpose to increase the solubility of the active.

The U.S. Pat. No. 6,355,272, protecting a mixture of lambda carrageenan and actives in the purpose to form granules. These granules can to be compressed (tablets) or filled in hard capsules (granules) or to form pellets (small beads). Therefore these different forms are gradually going to release over the time in the digestive tract, the active ingredients. Some others ingredients can be added like hydroxypropylmethylcellulose or hydroxypropyl cellulose.

The international application WO 0100177 concerning a combination of amoxycycline, a gum (cellulose, cellulose esters or ethers, xanthan gum and carrageenan) associated or not with phospholipids. The mixture is transformed under the form of tablets, capsules or granules for a prolonged release of the antibiotic.

And the Hercules' U.S. Pat. No. 6,358,525 protecting different hydroxypropylcellulose and hydrocolloid based compositions containing another polysaccharide selected from the group of guar, agar, algin, gellan, carrageenan, etc. . . . . These compositions are under the form of tablets in order to slow down the availability of the active substances to the organism.

In the same concept as for the oral route, sustained release systems have been developed for the intramuscular route: implants. These are small tablets placed under the skin slowly releasing the active due to the washing out of the physiological liquids (blood, lymph). Most of the actives are hormones.

Likewise skin can be a route for a slow release of an active. The programmed systems developed are patches or transdermal systems. A patch is a solid form more or less pasty, releasing the active like from a matrix, but this releasing depends of the solvent contained in the transdermal system which is going to increase the permeability of the skin. By this fact the active solubilized in this solvent goes through the skin and arrives in the blood circulation. Lot of applications have been developed: nicotine patches, scopolamine patches, isosorbide patches, etc . . . .

However these different forms, matrices, microgranules implants and transdermal systems have been conceived for a systemic action and not for a local treatment.

Contrary to the previous innovations, some solid forms slowly releasing actives for a local action, have been developed for the ocular and vaginal route.

In the case of the ocular route some forms are called Inserts. Different forms are actually commercialized like:

pre-cast hydrophilic matrices or hydrophilic lenses, which are considered as reservoirs because they are capable of being hydrated to nearly 85%. However the re-release of active ingredient contained in this reservoir is quite rapid.

erodable soluble implants impregnated with active ingredients (oval plates or pellets). Placed in the conjunctival cul-de-sac, they saturate quickly with lachrymal liquid. The liberation of the active ingredient is done by progressive dissolution of the support. A concrete example of this system is the hydroxypropylcellulose-based product Lacrisert®.

For the vaginal route most of the solid forms are tablets.

As previously, the tablets can very well offer a prolonged release in situ under the washing out of the vaginal secretions.

However the administration of such forms is not practical for the patient and a rejection may occur after a certain time, if the form itself does not show adhesive properties.

As an example, the PCT application WO2007035954 protects sustained release misoprostol tablets for the vaginal route where the cellulosic excipient possesses adhesive properties. By this fact the active ingredient is slowly release and can locally or systemically acts.

If solid forms permit to control more or less the release of an active all along the time, unfortunately their action is more systemic than local action.

The best form for a local action would be a liquid or pasty form. But here too, some difficulties appear.

Indeed to prolong the action of a liquid or pasty form at the local application site, is very difficult due to the fact that secretions of the mucous membranes are going to dilute the product under a perpetual washing out of these, like saliva, tears, nasal secretions, vaginal secretions, etc . . . .

Despite this difficulty some developments have been done in the field.

The first developments to increase the release time of a liquid or pasty form at the local application site are based on a physical transformation of the liquid form.

This physical transformation is called "in situ gel formation".

We understand by "in situ gel formation", a physical transformation of the cream or liquid under the physiological parameters like temperature of the body or the electrolytes and proteins present in the physiologic liquids, or pH of the secretions themselves. The physical transformation is an increasing of the cream or liquid viscosity. The viscosity increasing onto the targeted organ or membrane, permits, of cause, a slow release of the active under the washing out at the local application site.

Based on the in situ gel formation by complexation, reaction between formulation and ions or proteins of the secretion, lot of patents have been filed. Most of them are for the ocular route like soluble gels.

These slow down the release of the active ingredient because of their elevated viscosity. The viscosity prolongs the contact time of the active ingredient onto the cornea and in the conjunctival cul-de-sac. This intensification of the action is due to the slowing down of the elimination process in the lachrymal channel, due to the viscosity of the product.

These gels are generally developed with water-soluble polymeric molecules such as polyvinyl alcohol, cellulose derivatives, and acrylic derivatives.

As examples we can cite works done by:

Wang and Hammarlung (1) on gels of polyvinyl alcohol and of hydroxypropylmethyl cellulose containing homatropine hypobromite having a myotic effect.

Haas and Coll. (2) on methylcellulose gels containing pilocarpine.

Goldberg and Coll. (3) as well as those of Mandell and Coll. (4) and March and Coll. (5) on high viscosity acrylic gels containing pilocarpine hydrochlorate.

Schoenwald and Coll. (6) on Carbopol® gels containing prednisolone acetate

Other polymers can be used with the aim of delaying the release of the active ingredient such as alginic acid (Carteol® LP), and gellan gums (Timoptol®).

As examples:
the Japanese patent JP 2001501194 describes a liquid which is formed an in situ gel when it is applied, under eye drops, to the cornea. The Gelrite® component, a deactylated gellan gum forms an in situ gel by combination with the cations of the tears The U.S. Pat. No. 5,403,841 and EP 0424043, carrageenan gels seeing their viscosity increasing in contact with sodium ions or proteins contained in the tears.

The U.S. Pat. No. 5,965,152, describes anionic interactions between the miotic or mydriatic agent and a viscoelastic polymer like an anionic viscoelastic polymer and a cationic miotic or mydriatic agent. Placed in the eye, the cationic agent of the composition, may be released by displacement of endogenous sodium or potassium ions present in the tears. As an example the anionic viscoelastic polymer acid may be sodium hyaluronate or chondroitin sulfate, and the cationic agent may be the mydriatic agent atropine sulfate or the miotic agent pilocarpine. In this case the composition reacts like an exchange ion resin between the sodium of the tears and the active ingredient fixed on the viscoelastic polymer.

Likewise, based on the in situ gel formation by temperature elevation, different patents have been filed like:

U.S. Pat. No. 5,618,800 (Kabra et al.) protecting cellulose ether gels: viscosity increases under the temperature of the eyes.

U.S. Pat. No. 4,188,373, protects the polyoxyethylene-polyoxypropylene copolymer having a transition sol-gel temperature between 25° C. and 35° C. This means that under 25° C. the composition is liquid. Above 35° C. an in situ gel is formed The last in situ gel formation mechanism is based on pH sensitivity. As it is described in U.S. Pat. No. 4,136,173 the xanthan gum/locust bean mixture shows a liquid aspect at a pH between 3.5 and 5. Above 5, this mixture becomes solid.

The U.S. Pat. No. 4,474,751 combines all the in situ gel formation mechanisms described previously. Indeed the ingredient selected, the tetra ethylene diamine block copolymer of polyoxyethylene-polyoxypropylene reacts under temperature, pH and ions and becomes more or less liquid or viscous The second way to obtain a slow release at the local application site is achieved with bio-adhesive compositions.

By "bio-adhesive" we understand the capacity of a biological or synthetic material to "stick" onto a biological or mucous membrane.

The sticky effect of the bio adhesive composition comes from the fact the material is able to form chemical bonds with the substrate, the mucous membrane.

The most important bonds formed with the bio adhesive material, are Hydrogen bonds. It is a reaction which occurs between the OH groups of the bio adhesive material and the water of the secretion covering the mucous membrane.

Most of the studies realized in this field concern solid forms.

Indeed under the solid form the bio material shows stronger reaction with the substrate because the OH groups are totally available for forming hydrogen bonds. Under a liquid form the OH groups of the bio material are already combined with water decreasing by this fact, the potential to form hydrogen bonds with the substrate.

Under solid forms, for the ocular route some studies have been done using Carbopol® as bio adhesive material (HO-WAH HUI and Coll. [7]). But the bio-adhesion mechanism could not be perfectly established.

In the same way, some studies have been done for the nasal and vaginal route using, Carbopol® or derivatives of polyacrylic acid polymers, too.

As examples:
the U.S. Pat. No. 4,226,848 mentions the use of cellulosic derivatives and acrylic polymers as bio materials for the nasal route. The final product can be tablets, granules, powders.

The Japanese patent 130421/78 protects a polyacrylic acid polymer/hydroxypropylcellulose bio-adhesive mixture under a solid form for the vaginal route to treat a carcinoma.

These solid forms swell when they are in contact of the body fluid.

Compared with the latest, studies for the oral route, specifically the mouth, are more important.

The forms known as bio-adhesives for the oral route are mostly tablets or patches. The ingredients known as bio-adhesives tested within this application framework are:
Carbopol® (polyacrylates derivatives)
carboxyvinyl polymers and derivatives
hydroxypropylmethylcellulose and derivatives
Natural proteins from milk
gelatin
chitosan
and gum of acacia.

As examples the following patents can be cited:
MY125919 where the bio adhesive material is a mixture of cellulose, starch, lactose, water soluble polymer and a cross linked polycarboxilic polymer.

U.S. Pat. No. 6,977,083 where le bio adhesive material is a mixture of polyacrylates and sodium carboxymethylcellulose for a testosterone bio adhesive tablet.

WO 704342 where the bio adhesivity is obtained through a mixture of partly hydrolyzed PVP alcohol, polyethylene oxide, polyacrylates and hydroxypropylmethylcellulose.

Etc. . . .

However even if the tablets and the patches ensure a prolonged release of the active ingredient in any cavities, the maintenance during 8 hours of such forms in the mouth or in the vagina, is not conceivable for a patient.

Therefore liquids or pasty bio adhesive forms would seem better tolerated.

Under bio adhesive liquids or creams for vaginal, rectal and nasal routes, some patents have already been filed using approximately the same ingredients as those for the solid forms.

As example:
US Patent Publ. 2015/147282, US Patent Publ. 2014/186279 and EP0975331 protect a mixture containing a neutral diacyl lipid, a phospholipid, tocopherol and a biocompatible solvent. This mixture in contact the body fluid, like vaginal secretion, becomes bio adhesive by formation of lamellar structure where crystals are dispersed. The mechanism seems similar to an in situ gel formation, emphasized by addition of biomaterial. The prolonged release from these compositions can be counted by hours or by days.

HK1088829 and WO2004073597 protect a mixture containing particles of alginate dispersed in a non aqueous diluent, like glycerol or propylene glycol. In contact with body fluid, the particles swell, coalesce and stick onto the surface which can be the vaginal mucous membrane.

WO2005115339 has registered a liquid mixture containing a mucoadhesive ingredient, polyacrylic acid polymer, a permeation enhancer, phospholipids and a solvent having bio adhesive properties and which can be applied on nasal and vaginal membrane. The Applicant mentions that this mixture is polysaccharides free.

U.S. Pat. No. 6,465,626 and US Patent Publ. 2001/053359 protect compositions for nasal applications where the components are chitosan (bio adhesive material), gellan (in situ gel formation), and an alginate solution as suspending material for the gellan microsphere. Under the moisture of the nasal mucous, the particles swell and stick to the membrane.

U.S. Pat. No. 6,060,077 protects a vaginal bio adhesive liquid containing oestrogen as active, a Lipophile solvent (triglycerides), an hydrophilic gel forming agent chosen from carboxyvinylic acids, cellulose derivatives, gelatin, xanthan gum and guar gum, a gelling agent for the lipophilic phase (silica) and a hydro dispersible agent like polyoxyethylen glycol. This bio adhesive liquid composition is containing in a soft capsule. After its opening the liquid forms an emulsion onto the vaginal mucosa from which the active is slowly released. As the gelling agent shows bioadhesive properties, no flow is observed due to the gel fixation onto the mucosa. These properties can be increased by using buffer solutions. Indeed the Applicant considers that electrostatic bonds can be formed between the positive charges of the product and the negative ones of the mucous emphasized by the buffer solutions US Patent Publication 2003/180366 protects liposome compositions where the most important ingredient is phospholipid. These phospholipids are associated with hydrophobic material like oils in the purpose to form the barrier of the liposomes. To stabilize this barrier some polymers are added: cellulose derivatives or polyethylene, polypropylene polyurethane polyamide derivatives. Here too, this bio-adhesive composition is administrated to the vaginal cavity under soft capsule form. One of absorption mechanism described in this application is based on the Vander Waal bonds formed between the liposomes and the vaginal mucosa. This bending potentially conducts to a sustained release.

KR100292027 protects a bio-adhesive composition for the rectal route. The adhesive components are carbopol and polycarbophil associated with poloxamers and some other ingredients. The poloxamers have the property under temperature to become liquid. In this case the bio-adhesive properties of carbopol and the in situ gel formation mechanism are combined together.

WO9730693 protects compositions similar to the previous one. Instead of using carbopol or polycarbophil as bio-adhesive ingredient, they protect chitosan and alginate. It seems that the $NH_2$ groups of these excipients are going to react with the OH group of the poloxamer, permitting to adjust the in situ gelling temperature of the mixture. On the another hand, the OH group of alginate and chitosan react, too, to the oligosaccharides of the mucous increasing the bioadhesivity of the formulation.

U.S. Pat. No. 6,159,491 protects the use of a mixture of Carbopol® (Polycarbophil®), carrageenans and agarose highly purified in the purpose to have a release in two steps. In the present case the carrageenans are used as gelling agent, delaying the release of the active substances and Carbopol® as bio-adhesive.

U.S. Pat. Nos. 5,069,906 and 4,983,393 mention carrageenan as a matrix agent only, in the purpose to delay the release of the actives. The bio-adhesive character is not mentioned.

For the oral route, most of the developments have been done for the gastro intestinal tract.

Indeed we cite as examples:

U.S. Pat. No. 6,610,667 protects a composition of which the principal agent of bio-adhesion is alginate and at a lesser degree, other hydrocolloids such as the xanthan gum, galactomananes, glucomananes and carrageenans. The application is mainly centered around the combination alginate/gum xanthane or alginate/galactomananes or glucomananes. Furthermore, the esophagus is far from being a cavity easy to reach by hand.

GB 2324725 proposes compositions containing alginates and bicarbonate in purpose to cover the esophageal mucous (GB 2324725). The bio-adhesive material is alginates having a special grade defined by the mannuronic/guluronic ratio. This ratio permits to have a low viscous allowing the alginate gel to stick onto the gastro intestinal mucosa. The Applicant mentions that the alginates react with the mucin of saliva and gastro intestinal fluid, but does not explain how.

US Publ. 2003/198619 and WO03053400, protect a combination of polysaccharides (pentosan polysulfate), an enhancer (EDTA, Bile salt), a non ionic surfactant like Cremophor® and a viscosity reducing agent like polyethylene 5 castor oil. This bio adhesive liquid is contained in a soft capsule. After its opening in the gastric fluid, the bio adhesive liquid covers the stomach mucous membrane in purpose to increase the time release of the active. But more than a real bioadhesivity mechanism which can occur, it is an in situ gel mechanism which takes place.

The U.S. Pat. Nos. 5,672,356 and 6,242,004 mention the use of carrageenans as gelling agent delaying the release of the active ingredient, the bio-adhesion being supplied by the copolymer of methylvinyl ether and maleic anhydride.

Specifically applied on the mouth mucous, the patent publication US Patent Publ. 2007/189983 protects a tooth whitening composition having bio adhesive properties where the biomaterial are xanthan gum, carbomers and PVP copolymer. To maintain the active for a long time on the teeth a film forming agent is added, ethylcellulose. No mechanism of adhesion is described in the patent.

In an opposite way, the PCT application WO2007073346, protects a bio adhesive composition with a quick dissolution time in the mouth. The biomaterial is alginates. No mechanism of adhesion is described in this application.

Even if the bio adhesive liquid or pasty forms previously described, seem better tolerated by the patient, the washing out of the mucous membranes by the secretion conducts to a progressive dilution of the hydrogen bonds of the bio adhesive creamy product, decreasing by this fact, the time release at the targeted point.

Indeed under the water contained in the secretion, the strength of the hydrogen bonds towards the substrate decreases and slowly release the product from its targeted site. The product progressively loses its bio adhesive properties. This phenomenon is less important when the bioadhesive pasty forms combined hydrogen bonds with the substrate and the in situ gel formation mechanisms.

To overcome this problem, a stronger binding between the substrate and the liquid product must be needed.

One way is possible, the creation of stronger bonds (chemical or physical) with the substrate other than hydrogen bonds.

The US patent Publ. 2001/053359 describes different kinds of bonds other than hydrogen bonds, which can occur with the substrate: Van der Waals bonds, ionic bonds and polymer entanglement. The last is more a physical binding than a chemical binding.

Some patents touch on some potential combinations between the chemical groups of the bio adhesive material and the substrate, other than hydrogen bonds, like those previously cited:

WO9730693: interaction between $NH_2$ groups of the bioadhesive excipients and OH group of the poloxamer and between OH group of alginate and chitosan and oligosaccharides of the mucous U.S. Pat. No. 6,060,077: electrostatic bonds formed between the positive charges of the product and the negative ones of the mucous.

US Patent Publ. 2003/180366: Van der Waal bonds formed between the liposomes and the vaginal mucosa.

U.S. Pat. No. 6,391,294 describes different kinds of biomaterials, anionic and cationic, which are able to react together to form a bio-adhesive film on the body surface where the mixtures are applied. Among them carrageenan are cited. But U.S. Pat. No. 6,391,294 protects two liquids, one containing an anionic polymer, the other one, the cationic polymers. These two solutions must be applied simultaneously or a little differently in purpose to form the film by ionic interaction between the two polymers.

The carrageenan effectively possess a reactive group on its structure, a sulfate group ($SO_4^{2-}$), which is able to react with positive charged molecules like those containing an $N^+$. This property has been used for blocking the growth of some micro organisms rich in $N^+$ molecules.

This ability to form Van der Waals bonds between $SO_4^{2-}$ and positively charge molecules, has been already protected in two applications:

EP patent 125759 and the French patent FR 2542616 protect a gel to be applied on mouth and genital parties for curing candidosis. In these applications the carrageenan used is a denatured carrageenan in purpose to increase the number of sulfate groups which are going to react with the microorganism envelope rich in amines derivatives.

U.S. Pat. No. 5,658,893 protects a carrageenan liquid having the property to inhibit rotavirus infection. The sulfated polysaccharide interacts in the replication process of the virus due to the blockage of amine derivatives rich in N.

Thus, after a thorough study of the literature in the field of the bio-adhesive forms having a prolonged release, it has been unable to find a bio-adhesive pasty form combining different kinds of bonds with the substrate, other than hydrogen bonds and in situ gel formation, in the purpose to reinforce the adhesion of the liquid product to the substrate, specifically the mucous membranes. The aim of this reinforcement is to obtain a form having a prolonged release of long duration, greater than 2 hours.

Given this situation and to remedy it, the invention offers an original concept of viscous liquid compositions intended for the realization of pasty or liquid forms having prolonged action and/or release for local applications onto cavities easily reached by hand. These compositions are characterized in that long lasting and/or prolonged action and/or release of the active ingredient is obtained, not only by hydrogen bonds, but by chemical and physical reactions between the biomaterial and the components of the substrate, too. A film is formed at the surface of the mucous membrane, having reinforced bio-adhesive capacity. Under the effect of a permanent washing of the mucous membranes by the secretions, the action and/or release of the product or of the active entrapped in the aforementioned film, is greater than 2 hours and can be modulate by additives.

SUMMARY OF THE INVENTION

The invention relates to pasty or liquid compositions for applications on mucous membranes of cavities easily reached by hand, having a bio adhesive prolonged effect or release and comprising: i) a polysaccharide matrix agent selected from the group constituting of lambda carrageenan or iota carrageenan, allowing the in situ formation of a matrix film with a reinforced bio-adhesive capacity due to complexation reactions between the polysaccharide matrix agent and the components of the local secretions of the mucous membranes, ii) a lecithin compound as a reinforcing agent of the intrinsic bio-adhesive properties of the polysaccharide matrix agent, iii) a hydration medium for the polysaccharide matrix agent, iv) a lecithin co-solvent allowing the dispersion of the micellar lecithin solution in the hydration medium, v) additives vi) an active ingredient.

The purpose of the present invention is to realize in situ, after application of the preparation, a film having reinforced bio-adhesive properties, of which the action and/or release of the active ingredient is, as far as possible, independent of the pH and/or independent of the action of the secretions of the mucous membranes.

The reinforced bioadhesive properties are obtained by creation of chemical and physical bonds, other than hydrogen bonds, between the biomaterial and the components of substrate.

The reinforced bioadhesion is such that it is an instantaneous reaction with the substrate immediately after the matrix agent application on the mucous membranes.

DETAILED DESCRIPTION OF THE INVENTION

Figure 1:
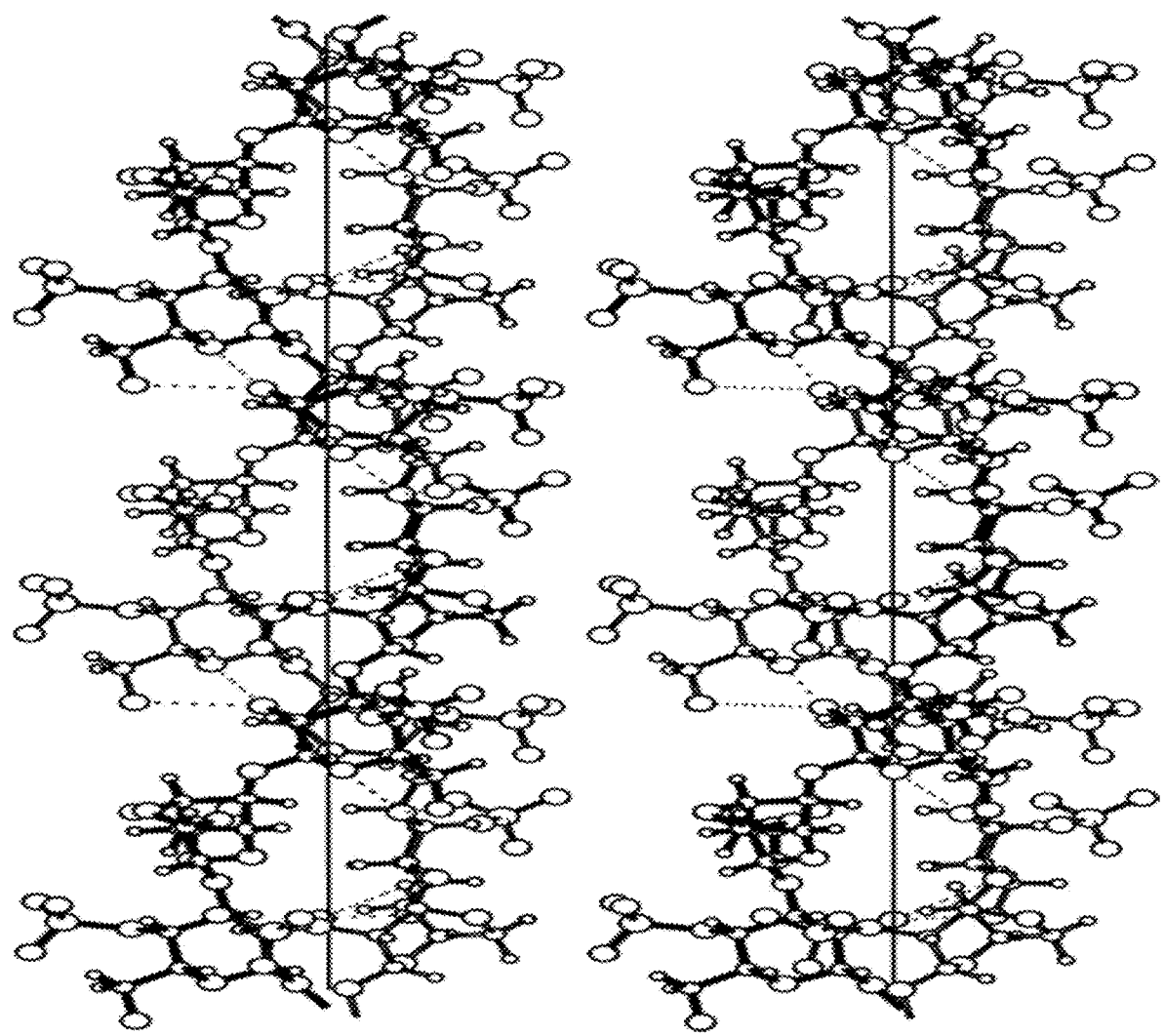
FIG. 1 shows the helical structure of different kinds of carrageenan.

By "polysaccharide matrix agent" we mean the polysaccharide alone, having bio-adhesive properties.

By "substrate" we mean all the mucous membranes easily reached by hand

By "bioadhesion" we mean the capacity of a biological or synthetic substance, the biomaterial, to "stick" to a biological or mucous membrane.

By "matrix agent" we mean the combination of three ingredients, a polysaccharide, lecithins, and a co-solvent, having both a synergic action towards the complexation reaction with the polymucossacharides of the mucous membranes By "co-solvent" we mean a liquid component permitting the dispersion or dissolution of an ingredient in another solvent where it is insoluble.

By "reinforced bio-adhesive capacity" we mean the capacity of the matrix agent to create supplemental bonds with the substrate, other than hydrogen bonds observed with the conventional bio-adhesive excipients.

By "matrix film" we mean the formation of a three-dimensional network, more or less solid, more or less thick, and more or less porous, in which is included the active substance.

By "biodegradable" we mean the degradation of a support generated by a biological mechanism such as the action of enzymes but also by a mechanical erosion mechanism due to the "washing out" secretions of the organism.

By "washing out" we mean a repeated passage of a solution on the same support until total exhaustion of the latter.

By "complexation" we mean the formation of a chemical or physical bond other than the hydrogen bonds encountered with the majority of the other agents known as bio-adhesives. This bond is characterized in that the energy is intermediate between the energy of a covalent bond and the energy of a hydrogen bond, such Van der Waals bonds or ionic interaction, thus leading to a structure more resistant to the phenomenon of "washing out".

This invention is applicable to the preparations intended for the oral mucous membrane, as well as the nasal, vaginal and rectal mucous membranes;

This invention is based on the fact that certain substances in the solid state or liquid state, have the property to form complex with certain molecules of the mucous membranes when they are applied to the latter. Depending on this substance, its property to complex is emphasized by the combination with some surfactants. Thus the matrix agent is tied to the surface of the mucous membranes, stronger than classic hydrogen bonds, forming a three-dimensional network from which the action and/or from which the active ingredient diffuses gradually over the time. This mechanism is similar to this of liposome absorption described in US Patent Publ. 2003/180366 already cited previously.

The surfactant permits a better contact between the biomaterial and the components of the substrate which can be react with the latter.

The biomaterial used in the present application has a natural origin, much used in the pharmaceutical, cosmetic and dietetic field.

This substance can be used alone and create a viscous film or a more or less solid structure, in which the active ingredient(s) are dissolved or dispersed.

This biomaterial can be used in combination with other excipients in the purpose of strengthening the structure of the aforesaid matrix film.

These excipients combined with the polysaccharide play the role of "binder".

By "binder" we mean substances acting as cements between the particles dispersed in a network in the purpose to agglomerate them and giving a more or less solid structure.

Thus, these binders avoid the dispersion of the active substances within the secretions of the organism by their entrapment in the viscous gangue or the spongy structure formed at the surface of the mucous membrane.

As a result, depending on the solidity of the obtained matrix film and the complexation of the matrix agent with the substrate, the action of the aforesaid film or the release of an active ingredient included in such system can vary between 1 to 48 hours according to the action site of the aforementioned preparation.

Preferably according to the present invention, the release time of the active ingredient is between 2 and 12 hours for the oral and nasal administration and the time release of the active ingredient is greater than 12 hours for vaginal administration.

The two components of the matrix agents allowing the formation the aforementioned films by complexation, belong to the class of the natural polymers, polysaccharides and to the class of amphiphile surfactants, the lecithins The polysaccharides chosen within the framework of this invention belong to the carrageenan family.

The carrageenans have been known for more than 600 years in the medical field and in the nutritional field in particular for their original property, which consists of gellifying milk by simply heating it.

They are polysaccharides, polymers of galactose more or less sulfated.

The carrageenans are extracted from different algae: *Chondrus crispus, Gigartina stellate, Gigartina acicularis, Gigartina skottsbergii, Gigartina pistillate, Gigartina chamissoi, Iridea, Eucheuma cottoni, Eucheuma spinosum.*

The extraction process used, leads to different types of carrageenans, the basic skeleton of which, is a chain of D-galactose residues alternatively bonded at $\alpha$-(I-3) and $\beta$-(I-4).

The different types of carrageenan are due to the quantity and the position of the sulphate groups onto the skeleton and to the presence or not of 3,6 anhydro bridge on galactose bonded at 1 and 4.

The proportion of the different sulphates groups and the anhydrogalactose bridge at 3,6 allowed isolation of different types of carrageenans. They are the iota-, kappa-, lambda-, beta-, nu-, and mu-carrageenans.

The lambda-forms exhibit many sulfurated groups compared to the kappa-forms. The iota-forms are intermediate.

The spatial structure of these different kinds of carrageenan is helicoidal, as shown in FIG. 1.

The mu- and nu-forms are in lesser quantities and are considered as impurities decreasing the gellifying effect of the iota- and kappa-forms.

The types of carrageenans retained for the present invention are the lambda- and the iota-carrageenans.

Compared to the kappa-carrageenans, the lambda- and the iota-carrageenans offer no syneresis phenomenon.

Lambda-carrageenans offer no gellifying properties, but thickening.

In the case of the iota-carrageenans, the gellifying property develops only if the preparation is subjected to heat.

Whether it is the iota- or the lambda-carrageenans, they are hygroscopic hydrocolloid substances due to the numerous OH groups present on the skeleton.

Resulting from the contact with the mucous membranes, these substances will have the possibility to develop bio-adhesive properties like the conventional bio-adhesive excipients such as Carbopol® or carboxymethylcellulose defined as polymers suitable for forming more or less solid three-dimensional networks onto mucous membranes, too.

The bio-adhesive properties of these excipients come from the fact the skeleton of these polymers brings lots of OH groups like carrageenans The conventional bio-adhesive mechanism of the excipients known as bio-adhesives is defined as being an interaction of the aforesaid excipient with water of mucus covering the mucous membranes of the cavity. This mucus is generally highly hydrated and has a certain viscosity due to the presence of mucin.

The composition of mucin differs from the site of its action. Indeed mucin from saliva is different from vaginal secretion or tears, etc. . . . . .

Figure 2:
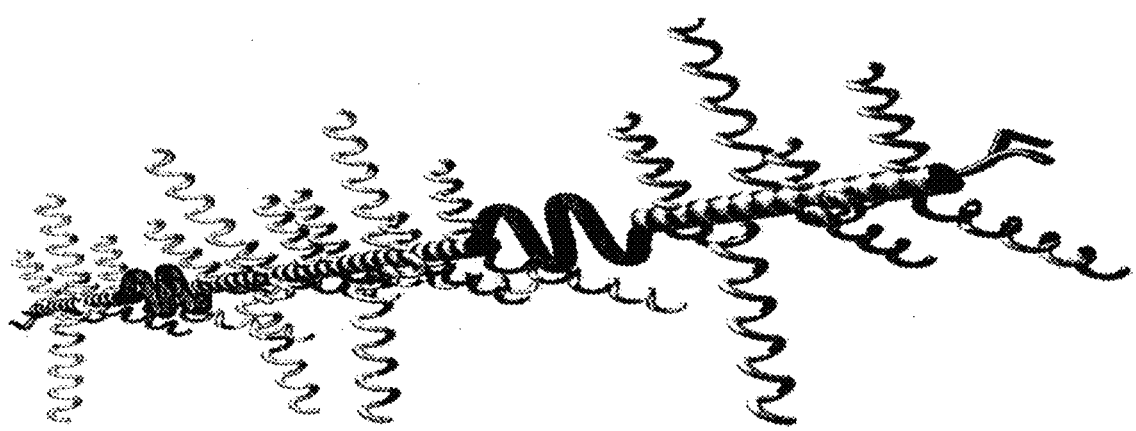
FIG. 2 shows a glycoprotein or oligosaccharide with a very complex structure.

As shown in FIG. 2 the mucin is a glycoprotein or oligosaccharide with a very complex structure having:
  (a) A polypeptide backbone (10 to 30%): repeat units of serine, threonine and proline,
  (b) carbohydrate side chains: monosaccharides including N-acetylglucosamine, N-acetylgalactosamine, galactose, fucose and sialic acid
  (c) N and C terminal end, and
  (d) cysteine rich domains (hydrophobic patches)

Thus, according to their chemical nature, the conventional known bio-adhesives are hydroscopic. In contact with the mucous membranes, they expand quickly with formation of hydrogen bonds between their hydrophilic groups and those of the mucus water and inter alia those of mucin. Consequently there is formation of a three-dimensional network from a polymer/mucin interaction.

However, the hydrogen bonds are bonds of weak energy. Consequently a dilution of the medium or the constant "washing out" of a substrate will lead to a rapid breaking of these bonds thus decreasing the bio-adhesive character of these excipients.

On the other hand, in the case of iota- and lambda-carrageenans, the bio-adhesive character is known as "reinforced" because, besides the creation of the hydrogen bonds observed with the conventional excipients, other bonds are formed with the support.

The first one is based on electro attractivity of the molecules. Indeed, it has been noted that the iota- and lambda-carrageenans possess sulphate groups on the molecule skeleton. These chemical groups are very reactive and create complexing reactions with certain molecules having free protons on some of their atoms such as nitrogen and sulphur. Because of the presence of these free protons, $N^{2+}$ or $S^{4+}$, anionic groups, such as the sulphate groups of the carrageenans, $SO_4^{2-}$, react very strongly with these molecules.

As it has been previously said, mucin shows lot of positively charged N and S groups, so the electro attractivity between carrageen and mucin can occur. The bond energy of these one is stronger than this of a simple OH bond. These are called Van der Waals bonds.

The second one is based on the physical structure of the molecules. Indeed carrageenan possesses a helicoidal space structure. In front of another molecule having an helicoidal space structure, even partially, like mucin, the two molecules are going to be overlapped creating new bonds reinforcing the structure formed by hydrogen bonds and Van der Waals bonds Thus, mucin and of the mucous membrane, having in both cases nitrogen atoms, in contact with, the iota- and lambda-carrageenans, will create a three-dimensional network constituted:
  by hydrogen bonds formed between the OH groups of polysaccharide and those of mucin and the water present in mucus,
  by Van der Waals bonds between the sulphate groups of polysaccharide and the nitrogen atoms of mucin and the mucous membrane,
  and by structure interaction between the helicoidal parts of each molecule.

The "reinforced" bio-adhesive character has been revealed by a comparative study between Carbopol® 934P NF and the lambda-carrageenans (Benvisco® LPB 2301), using a washing test method.

Contrary to all the studies carried out on the bio-adhesivity using a stainless steel support, the studies of the bioadhesivity of these two solutions has been carried out on biological cellulose membrane (osmotic membrane) impregnated with a pH 6.8 phosphate buffer solution or a 5% mucin solution in a pH 6.8 phosphate buffer.

This test is based on the washing out of two cellulosic membranes fixed on a solid support. After impregnated the membranes and the deposits done, the support is fixed on the arm of the disintegrating apparatus instead of the basket used for tablet disintegration test as described at the European Pharmacopeia. The "washing out" of these deposits is carried out by using the tablet disintegration apparatus described in Pharmacopee Europeenne, $4^{th}$ edition.

The arm is immersed in a beaker containing water or buffer solutions and describes a backward and forward motion from top to bottom at the ratio of 30 per minute and with an amplitude of 12 cm.

Two aqueous solutions have been realized containing, respectively, 2.0% of carrageenan and 0.6% of Carbopol®. These concentrations have been chosen because the viscosity of each final solution is identical. This avoids the influence of the viscosity during the test.

Something must be to take into account to understand the following results. Indeed the liquid-based carrageenan preparations are characterized as Newtonian products that is to say that they flow freely under the effect of their mass only, which is not the case of Carbopol.

Furthermore, these same products are also characterized as thixotrope solutions, that is to say, that these aforementioned solutions, having the appearance of a solid at rest, rapidly liquefy, under the effect of an agitation. This property is not observed with Carbopol, too.

Thus, after deposit of the carrageenans solution at the surface of the wet membrane, this flow has been clearly observed when the membrane support is fixed vertically on the arm and during its motion. Nothing like this is observed in the case of Carbopol®. Its flow was clearly less pronounced after activation of the apparatus than this of carrageenan gel.

The impregnation of the membranes is done 30 seconds before the deposit of the solutions.

The impregnation of the membrane is such that a liquid film is formed at the surface of the latter simulating, therefore, what occurs at the surface of the different mucous membrane: wetness of the mucous membranes.

But in the case of the membrane impregnated with a pH 6.8 phosphate buffer solution alone, instead if forming a film the membrane absorbs the liquid and becomes humid.

Using a 5% mucin buffered solution for impregnating the membrane, a liquid film is formed at the surface of the membrane due to the viscosity of the impregnated solution.

0.5 ml of each solution to be tested is deposited at the surface of this impregnated membrane, at 6 cm from the inferior edge.

The "reinforced" character of the bio-adhesivity is tested by "washing out" the deposit in a pH 6.8 buffered medium simulating the different secretions of the organism.

This is done by determination of a time release of each gelled solution and on each kind of impregnated membrane.

Indeed, the disintegration apparatus as well as a chronometer are activated when the deposit surplus of carrageenan solution begins to drain to the inferior part of the membrane, letting a film on the membrane. In the case of Carbopol® solution, no flow of the deposit is observed.

By this fact the quantity of carrageenan covering the membrane is less than this of Carbopol®

Two studies have been conducted, one with membrane impregnated with pH 6.8 buffer solution and the other with membrane impregnated by the mucin solution.

impeded in its flow and, thus, driving the effectuated deposit with it.

This bio-adhesive property has also been demonstrated by recording the flow times of a carrageenan-based solution on a 45°-inclined plane covered with the same biological membrane impregnated or not impregnated with mucin. This test is called the flowing test.

Significant time differences have been noted between the flow on buffer impregnated membrane and mucin impregnated membrane.

TABLE 2

| Carrageenan concentration | Buffer membrane (flow time) | Mucin membrane (flow time) | Aptitude to the adhesion $F_{aa}$ | | Bio-adhesivity factor $F_{ba}$ | |
|---|---|---|---|---|---|---|
| | | | Data | Mean | Data | Means |
| 2% | 38" | 54" | 16" | 12" | 1.42 | 1.31 |
| | 43" | 52" | 9" | ±3" | 1.21 | ±0.11 |
| | 41" | 53'" | 12" | 28.47% | 1.29 | 8.11% |
| 3% | 5'52 | 7'58 | 126" | 122" | 1.36 | 1.34 |
| | 5'59 | 8'01 | 122" | ±3" | 1.34 | ±0.02 |
| | 6'03 | 8'02 | 119" | 2.87" | 1.33 | 1.13% |
| 5% | 17'58 | 22'05 | 247" | 251" | 1.23 | 1.23 |
| | 17'59 | 22'14 | 255" | ±4" | 1.24 | ±0.005 |
| | 18'08 | 22'19 | 251" | 1.59% | 1.23 | 0.47% |

Contrary to all expectations, a stronger bioadhesivity is observed for lambda-carrageenans in contact with the membrane impregnated with 5% mucin solution.

Indeed in Table 1, shows that on the buffer impregnated membrane only, the two bio-adhesive solutions have the same time release from the support.

But on the 5% mucin impregnated membrane a significant difference of 2 minutes 36 seconds (±12'36") is observed between carrageenan gel and Carbopol® gel.

This difference in favor of carrageenan solution is unexpected due to the fact that the quantity of the material at the deposit site is less than this of Carbopol, this one having not flowed before the switch on of the apparatus.

The result is more remarkable due to the fact the Carbopol deposit has had more time to create hydrogen bonds with the substrate, not flow having been not observed from the deposit site, in opposite to this of carrageenan.

The time difference observed for the bio-adhesive results between the buffer impregnated membrane and those of the mucin impregnated membrane comes from the fact that the mucin solution formed a fluid film at the surface of the membrane and immediately flows when the apparatus is switched on.

TABLE 1

| | Buffer impregnated membrane (time release) | Mucin impregnated membrane (time release) |
|---|---|---|
| Lambda-carrageenans | 9'43" ± 0'47" | 8'52" ± 0'16" |
| Carbopol ® | 9'29" ± 0'43" | 6'52" ± 0'9" |

Surprisingly, it seems that the mobile liquid film at the surface of the mucin impregnated membrane, free of all flow in vertical position, sees its flow impeded by the presence of the carrageenans at its surface.

In the case of Carbopol®, an opposite result is observed. The liquid film at the surface of the membrane is not Despite the fact that iota carrageenan possess sulfate groups, too, it is preferable to select lambda carrageenan due to its higher concentration of sulfate groups than iota carrageenan.

Moreover, different kinds of carrageenan exist on the market, like those mentioned in the French patent FR2542616 or EP 0125759 where degraded carrageenan iota and kappa are used for better film forming properties. Using these kinds of carrageenan in the present application will decrease their bioadhesivity properties due to the partial destruction of the helicoidal space structure avoiding the entrapment between the helicoidal structure part of the mucin and this of carrageenan. Therefore in a prefer embodiment, lambda carrageenan used in the present application is not modified or denaturized after its extraction from algae.

Despite the carrageenans being the object of a certain number of patents in more diverse fields other than pharmaceuticals, cosmetics, and dietetics, they are, however, less used for the realization of sustained release forms and even less for the realization of bio-adhesive systems having a prolonged release.

Some patents other than those previously cited, have been filed for special pharmaceutical applications.

It is the case of the patent applications US Patent Publ. 2004/019010 and WO2002/040056 where carrageenan are used under a gel form in the purpose to substitute the vitreous humour of the eye during ocular surgeries, such as cataract. The vitreous humour is replaced by these gels which, gradually over time, see their viscosity diminished to avoid an excessively strong intra-ocular pressure. These gels can be combined with active substances such as anti-inflammatory drugs, antibiotics, etc, which thus avoid any post-operative complications.

Likewise the International Application WO2004/075920 protects carrageenan as vector of active ingredients in the pulmonary area with the aim of delaying their release. Here also, the lungs are far from being considered as a cavity easily reached by hand in the same manner as the oral, vaginal, or rectal. Furthermore, the pulmonary secretions are less substantial than those observed on mouth or cornea.

Other patents such as patent EP1452168 concern skin applications of the carrageenans. The patent application US Patent Publ. 2002/071861 protects the use of the carrageenans but the bio-adhesive aspect of these preparations is supplied by carboxymethylcellulose, hydroxypropylmethylcellulose and Carbopol®.

More than this, skin is not considered as a cavity and the moisture covered it is much more less than the others cavities.

In the present invention, according to the zone treated, the concentration of lambda carrageenans, in the medium varies from 0.5% to 30% in relation to the final mass of the preparation.

The second ingredient of the matrix agent is a surfactant belonging to amphiphile surfactants: lecithins.

Lecithins are mixture of different phospholipids.

As showing in FIG. 2, phospholipids are characterized by two poles:
- an hydrophilic pole containing phosphate groups ($PO_2^-$) and nitrogen groups ($N^+$) depending of the nature of the phospholipids
- and a hydrophobic pole containing fatty molecules These compounds are natural ingredients extracted from eggs, soya beans, etc. . . . . They are components of the membrane cells. They are well-known in pharmacy, cosmetic and food for their emulsifying properties. In a biphasic solution (water and oil) they give a well organized structure, hydrophilic head still turns to water. The most well-known structure using these properties are liposomes, those described in US Patent Publ. 2003/180366.

Figure 3:
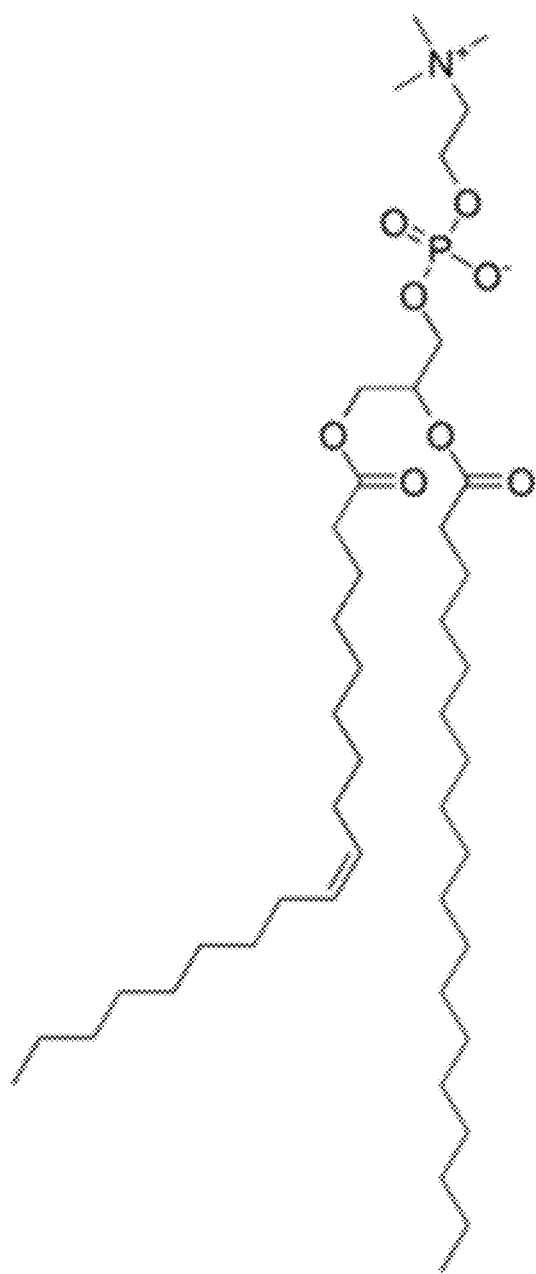
FIG. 3 shows a fatty molecule with an unsaturation showing a break in the linearity of the molecule.

Depending on the nature of the fatty molecule of the hydrophobic pole, the size of this one is more or less long. Moreover if the fatty molecule is more or less saturated, the linearity of the hydrophobic pole is modulated. With an unsaturated fatty molecule the linearity decreases. A break in the linearity is observed like in FIG. 3.

Depending on the purity of the phospholipids these can be in a powder form (highly purified) or a liquid form (less purified).

Phospholipids under liquid form are a mixture of oil and phospholipids like soya bean phospholipids and soya bean oil.

Depending on the nature of the hydrophilic pole, different kinds of phospholipids exist: phosphatidylcholine, phosphatidylserine, phosphatidylethanolamine, phosphatidylinositol and phosphatidic acid.

Better than phospholipid itself a mixture of different phospholipids, called lecithin, is preferable.

These oily liquid mixtures are obtained from different oilseeds like soya bean, sun flowers, and rape seeds or from egg yolk.

The phospholipid concentration in lecithins differs from the oilseeds and the process used to extract these latter.

Lecithins are not miscible to water. They swell, forming a colloidal suspension.

This has been observed when an aqueous carrageenan solution has been mixed to liquid lecithin. Despite the fact that carrageenan are generally used to stabilize an emulsion, a biphasic liquid form is obtained in this case.

The most preferable way to incorporate lecithins to a carrageenan solution, is to use a co-solvent.

Among all the existing solvents, the co-solvents retained for this application, are alcohols, like ethyl alcohol and the polyols like glycerol.

The co-solvent permits, first, to progressively incorporate water in the liquid lecithin, until a phase inversion.

By "phase inversion" we mean the passage from an oily emulsion (W/O) to a aqueous emulsion (O/W) without phase separation.

Under this state, the liquid looks like a more or less yellow milky solution where lecithins are well dispersed under a form of micelles due to their chemical structure.

This phase is required to permit the best dispersion of lecithins in the aqueous solution of carrageenan without observing phase separation during the time.

It is remarkable that the best dispersion is obtained for a ratio lecithin/co-solvent minimum equal to 1:0.8.

Indeed, under this value, despite the fact that lecithin is well dispersed in water and the phase inversion occurs, the dispersion in carrageenan solution is not reached. A biphasic solution is formed.

The most preferable lecithin/co-solvent ratios is minimum equal to 1:1;6.

Surprisingly combined to lambda carrageenan, lecithins under a micellar solution emphasize the bio adhesive properties of these polysaccharides.

Indeed, using the flow test as previously described, the lecithin increases the bio-adhesive capacity of the carrageenans in a significant manner. For a same viscosity and a lesser concentration, the difference of flow time on mucin impregnated membrane and on buffer impregnated membrane is around 414 seconds. Without phospholipids this difference is only 122 seconds.

TABLE 3

| Viscosity | Carrageenan Concentration | Lecithin Concentration | Buffer membrane (flow time) | Mucin membrane (flow time) | Aptitude to the adhesion ($F_{aa}$) | | Bio-adhesivity factor ($F_{ba}$) | |
|---|---|---|---|---|---|---|---|---|
| | | | | | Data | Mean | Data | Means |
| 2533 cPs | 2% | 5% | 9'38 | 17'11 | 453" | 414" | 1.78 | 1.72 |
| | | | 9'54 | 15'31 | 337" | ±67" | 1.56 | ±0.14 |
| | | | 9'12 | 16'46 | 454" | 16.22% | 1.82 | 8.13% |
| 2625 cPs | 3% | 0% | 5'52 | 7'58 | 126" | 122" | 1.36 | 1.34 |
| | | | 5'59 | 8'01 | 122" | ±3" | 1.34 | ±0.02 |
| | | | 6'03 | 8'02 | 119" | 2.87% | 1.33 | 1.13% |

The "washing test" study confirms the synergy between carrageenan and lecithins 4 solutions have been realized for this study:
(a) 2% of carrageenan alone in water
(b) 2% of carrageenan and 12% glycerol (co-solvent) in water
(c) 2% of carrageenan, 7.5% of lecithin and 12% of glycerol, in water (d) 7.5% of lecithin, 12% of glycerol in water (micellar solution)

0.2 ml of each solution have been tested on buffer impregnated membrane and on mucin impregnated membrane. Time to wash the membrane is measured. All the results are mentioned in the table below.

No surprise with the micellar lecithin solution (d). This one does not show bio adhesive properties.

But all the solutions containing carrageenan, (a), (b) and (c) show bio adhesive properties, more or less significative between (a) and (b), but strongly significative between solution (c) and the two others.

TABLE 4

|  | Buffer membrane (time release) | mucin membrane (time release) |
|---|---|---|
| 2% carrageenan | 2'03 ± 0'01 | 7'54 ± 0'54 |
| 2% carrageenan - 12% glycerol | 1'04 ± 0'02 | 9'37 ± 0'32 |
| 2% carrageenan - 7.5% lecithin - 12% glycerol | 3'10 ± 0'13 | 14'27 ± 0'10 |
| 7.5% lecithin - 12% glycerol | <5 sec. | <5 sec. |

Combined with carrageenan the lecithins increase by 2 the bio adhesive properties of the formulation.

Physically it has been observed the formation of aggregates between the mucin and the matrix agent (carrageenan/lecithins) well fixed on the membrane.

Therefore this synergy results from:
hydrogen bonds formation between the matrix agent (carrageenan/lecithin), and the secretion, more exactly, between hydroxide groups (OH) of carrageenan, hydroxide groups and nitrogen groups ($N^+$) of lecithin, and the secretion water.

and the combination of the matrix agent (carrageenan/lecithin) with mucin by overlapping between the helicoïdal structures of mucin, carrageenan and somewhere of lecithin.

Other studies have been done to show the synergic effect of lecithin by substituting them with other surfactants other than amphiphile surfactants, like polysorbate 80 and sodium laurylsulfate.

Two solutions have been realized where lecithins have been substituting by polysorbate and sodium laurylsulfate:
(e) carrageenan at 2% concentration+7.5% concentration of polysorbate 80+12% concentration of glycerine in water, solution
(f) carrageenan at 2% concentration+7.5% concentration of sodium laurylsulfate+12% concentration of glycerine in water, solution The results in the Table 5 below are remarkable: no synergic effect with other surfactants.

TABLE 5

|  | Buffer membrane (time release) | mucin membrane (time release) |
|---|---|---|
| 2% carrageenan | 2'03 ± 0'01 | 7'54 ± 0'54 |
| 2% carrageenan - 7.5% phospholipid - 12% glycerine | 3'10 ± 0'13 | 14'27 ± 0'10 |
| 2% carrageenan - 7.5% polysorbate 80 - 12% glycerine | 2'27 ± 0'10 | 7'06 ± 0'36 |
| 2% carrageenan - 7.5% sodium laurylsulfate- 12% glycerine | 2'13 ± 0.05 | 5'06 ± 0'30 |

The preferred lecithins for this application are extracted from seed of soya bean, sunflower, rapeseeds, cottonseeds and from eggs, milk and marine sources.

The quantity of these substances used to increase the bio-adhesive capacity of the carrageenans can vary from 0.1% to 50% in weight in relation to the total mass of the excipients.

In parallel the co-solvent concentration must be related to the lecithin concentration for a minimum ratio equal to 1:0.8, more preferable 1:1.6.

The co-solvent are selected from the group of alcohols, ethanol, propanol, butanol, and from the group of polyols like glycerol, propylene glycol, polyoxyethylene glycol.

The hydrating solvent of the polysaccharide matrix agent, especially carrageenans, can be aqueous or hydro-alcoholic. The proportion of the alcoholic phase can vary from 10% to 90% in mass in relation to the total mass of the hydrating phase.

The alcoholic phase can be embodied by ethylic alcohol and isopropyl alcohol.

The addition of certain ions permits to obtain a better hydration of the carrageenans and at the same time, increase their concentration in the medium.

The agents supporting this hydration belong to the class of alkaline and the alkaline-earths ions. They are inter alia:
sodium and potassium salts of hydrochloric, sulphuric, nitric, phosphoric, citric acids and derivatives,
and potassium and sodium hydroxides.

The proportion of alkaline and alkaline-earth ions which can be added to the medium varies between 0.001% to 50% in mass in relation to the total mass of the preparation.

The hydrating phase of carrageenan can be buffered to secure the stability of the active substances but also, this of the polysaccharide matrix agent.

Indeed, the carrageenans mixed with dextrose, in neutral medium, undergo progressive hydrolysis in time, increased by the action of heat.

It is thus that in neutral medium and on a 24 hour period, it is observed a reduction in the viscosity of the product by a progressive hydrolysis of the carrageenans releasing acid radicals in the medium.

Within the acid framework of buffer solutions, the compositions can be as follows:
sodium hydrochloric/chloride acid or potassium hydrochloric/phtalate acid or hydrochloric/glycocolle acid buffer.
citric acid/citrate or citric acid/sodium hydroxide buffer.
lactic acid/lactate buffer.

The proportion of the different components permits maintaining an acid pH ranging between 2 and 5.

In another hand, a good carrageenan stability is observed in neutral or basic medium.

The buffer solutions that can be thus used, respond to the following compositions:
phosphate buffer: sodium or potassium phosphate
carbonate buffer: bicarbonate/carbonate
phthalate buffer: potassium/hydrochloric acid diphthalate
borate buffer: boric acid/sodium borate The value of the pH of the buffered medium can vary from 5 to 12.

The present invention is related to the administration of a certain number of active substances.

The active substances that can be used in such a form, belong to certain pharmacological categories, namely analgesics, anti-inflammatories, antispasmodics, cytotoxics, antibiotics, antifungals, disinfectants, pesticides, hormones, antivirals, antimigraine agents, anti-allergics, analeptics, respiratory agents, spermicides, anti-hemmorrhoidal agents, vasoconstrictors, vasodilators, antipruritics, uterorelaxants, antiglaucoma agents, mydriatics, and antiasthmatics.

These substances can be dissolved in the hydrating phase of the polysaccharide matrix agent, or in the solid state, dispersed in the hydrating polysaccharide matrix agent.

Despite the fact that a certain number of these substances can be solubilized in the hydrating phase of the carrageenans, others can require a solubilization in an organic phase.

Among all organic solvents usable without danger to the human organism; some are retained:
- vegetable oils, hydrogenated vegetable oils, ethoxylated vegetable oils: olive oil, hazel nut oil, coconut oil, castor oil, soy oil, sesame oil, etc.
- mineral oils: paraffin, isoparaffin, cycloparaffin, silicone oils, isohexadecane, isododecane, and derivatives, etc
- natural oils, squalane, hexamethyltetracosane, the mono-, di- and triglycerides, etc.
- synthetic oils: polyisobutene, hydrogenated polyisobutene, etc.
- and other solvents: ethanol, propanol-1, propanol-2, polypropylene, propylene carbonate, dimethyl isosorbide ether, polyoxyethylene glycols (Macrogols), glycerol, fatty acid esters of polyethylene, fatty acid esters of propylene glycol, dicaprylate/dicaprate esters of propylene glycol, caprylate/caprate esters of glycerol, fatty acid esters of polyoxyethylene/polyoxypropylene glycol, triacetin, isopropyl myristate, glycofurol, liquid fatty acid esters, ethyl acetate, butanol, propylene glycol acetate, butyl acetate, ethylene glycol monobutyl ether, ethyl lactate, butyl acetate, diethylene glycolmonoethyl ether, glycerin monooleate, glycerin linoleate, fatty acid glycerol esters, fatty acid esters of glycerol and PEG etc.

The proportion of these different solvents, used in these preparations, depends on the solubility of the active ingredients and can vary from 0.01% to 50% in volume in relation to the total mass of the hydrating phase.

Sometime these oily phases containing actives can require another surfactant, other than the micellar solution of lecithin, to be well emulsified with the hydrating phase.

Among all the existing surfactants which can be associated to the micellar lecithin solution, for preventing a phase separation, those which have been selected are:
- nonionic surface-active agents:
- sorbitan esters: polysorbates, Spans, Tweens, etc. . . .
- polyethoxylated fatty acids: stearate of PEG-8 stearate through stearate of PEG-100;
- polyethoxylated fatty alcohols: mixtures of monolaurate ethers of PEG having from 4 to 23 oxyethylene groups in the polyoxyethylene chain, etc. . . .
- glycol esters: methylglycol stearate;
- glycerol esters: glycerol monostearate, PEG-75 stearate, glycol and PEG 6-32 stearate, etc. . . .
- PEG esters;
- saccharose esters;
- fatty alcohol and PEG ethers: Brij;
- ethers of alkylphenols and PEG;
- surface-active agents having an amid function:
- monoethanol amides of coprah fatty acids, monoethanol amide of lauric acid, etc. . . .
- diethanolamide of myristic acid, of lauric acid, etc. . . .
- monoisopropanolamide of lauric acid.
- the ionic surface-active agents:
- sulphate derivatives: sodium laurylsulfate and its derivatives;
- sulphonated derivatives: sodium dodecylsulfosuccinate and its derivatives;
- amphoterics: coprah alkyldimethylammonium betaines, fatty acid amides with betaines, lauryl-α-iminodiproprionic acid and its derivatives, lauryl-myristyl-α-aminoproprionic acid and its derivatives, etc. . . .

The surfactant concentrations which can permit a good physical stability of the final product can vary from 0.01% to 50% in weight in relation to the total mass of the hydrating phase.

Besides the fact that the active ingredients can be solubilized in the hydrating phase or in another solvent, these can also be incorporated in the solid state creating a bioadhesive suspension.

As a result, the active ingredients must satisfy a particle size criterion.

Thus the granulometric distribution of the powders can spread from 1 μm to 1000 μm, preferably ranging between 1 μm and 250 μm.

As it has been demonstrated through different trials, the matrix agent creates a viscous film onto the mucous membrane.

The viscosity of this film can be more or less stronger by introducing in the medium, substances which are going to increase the solidity or not, of this network.

Many substances can play this role. But only the starches have been retained, in particular their derivatives, because they are products that are more or less soluble in the hydration phase strengthening, by this fact, the film structure due to their aptitude to form viscous networks by swelling in contact with the water.

Thus the native starches are retained as structuring agents in the aforementioned invention as well as their derivative products resulting from:
- physical modifications: pre-gelatinization
- chemical modifications:
- chemical or enzymatic dextrinisation reaction
- acid hydrolysis
- oxidation reaction
- substitution reaction by:
- phosphoric acid
- adipic acid
- acetic acid
- hydroxypropyl or hydroxyethyl groups.

These different structuring agents can be obtained from starches of wheat, rice, corn, manioc and potato.

The starch quantities used in order to obtain an action and/or a release of the active ingredient between 2 and 48 hours can vary from 0.01% to 50% in mass in relation to the total mass of the preparation.

Their property to swell into the contact of water, will be better if their particles size are fine. Thus the particle size of the starches and modified starches making such results attainable must range between 1 μm and 1000 μm with a preference for a size ranging between 1 μm and 100 μm.

Preservation additives and dyes can be introduced into the composition.

The proportion of preservative can vary from 0.0% to 10% in mass in relation to the total mass of the preparation.

The dyes can be water-soluble or fixed on alumina lacquer or another support.

The optimum percentage of required dye ranges between 0.01% and 5% in mass in relation to the total mass of the preparation.

In the case of preparations intended for the oral cavity, moistening agents can be added to the bio-adhesive composition.

By "moistening" we mean substances that bring a certain moisture to the medium in which they are located. This is due to their intrinsic hygroscopic properties, namely fixation of the moisture of the surrounding atmosphere moisture.

Among these substances are the polyols, such as glycerin, sorbitol, maltitol, xylitol, mannitol, etc.

These products can be used with a concentration ranging between 1 and 30% in mass in relation to the total mass of the liquid phase.

In these preparations being intended to be applied to the oral mucous membrane, flavors as well as sweetening substances can be added The flavors can be natural or synthetic, the same for the sweetening substances.

Besides saccharose conventionally used as a sweetening substance, aspartame, acesulfam, sodium saccharin and sodium cyclamate can be retained as sweetening agents.

Depending on the sweetening substance used, the concentration in the medium can vary from 0.1% to 30% in mass in relation to the total mass of the preparation.

The solutions or suspensions thus realized, creating in situ matrix film with prolonged release, have viscosities going from 100 mPa and 500,000 mPa.

These solutions or suspensions can be packaged:
in multidosage vials: bottles or tubes
in single dose: unidose, Bottle-Pack®, nozzle tubes having single use
in spray: liquid spray or foam formation Such bio adhesive compositions, after application, lead to an action and/or a progressive release of the active ingredient over a period that can go from 1 hour to 48 hours, this kinetic release being, little or not, dependent on surrounding biological factors. This dissolution kinetic can be of the order of zero or 1, depending on the type of excipients used to obtain such a release.

Besides the use of these bio-adhesive compositions within the framework of a prolonged release of an active within a cavity, these same systems, in the absence of any therapeutic molecule, are of interest from a mechanical standpoint and, inter alia, regarding the lubrication of the mucous membranes when these are subject to dryness, such as oral dryness in the oligoptyalism, vaginal dryness, nasal dryness in the case of Sjôgren disease.

Indeed, these compositions by consequence of the intrinsic lubricating character of the carrageenans and the combination with a micellar solution of lecithins, being amplifiable by the incorporation of mineral or vegetable oils, or surface-active agents, allow maintenance of a lubricating action over an 8-hour period.

The examples of preparations appearing hereafter are possible composition formulas according to the present invention and they do not limit it in any way.

Example 1: Anti-Snoring Bioadhesive Composition

| | |
|---|---|
| Lambda Carrageenan | 2.08% |
| Sodium methyl paraben | 0.08% |
| Sodium propyl paraben | 0.02% |
| Lecithin (Soya bean) | 5.00% |
| Extrait reine des prés | 3.00% |
| Alcohol 95% V/V | 4.00% |
| Cynorrhodon | 2.07% |
| Aspartam | 0.07% |
| Mint flavor | 3.00% |
| Demineralized water QS | 100% |

Example 2: Lubricating Bio-Adhesive Gel for Oligoptyalism

| | |
|---|---|
| Lambda-carrageenans | 3.00% |
| Lecithin (Soya bean) | 5.00% |
| Glycerine | 8.00% |
| Preservatives | 0.10% |
| Mint flavor | 0.02% |
| Aspartame | 0.01% |
| Demineralized water QS | 100% |

Example Number 3: Hydrating Bio-Adhesive Vaginal Gel

| | |
|---|---|
| Lambda-carrageenans | 2.00% |
| Lecithin (Soya bean) | 7.5% |
| Glycerine | 12% |
| Hyaluronic acid | 2.50% |
| Paraffin oil | 1.00% |
| Auto-emulsionable glycerol monostearate | 8.00% |
| Sodium methyl parahydroxybenzoate | 0.08% |
| Sodium propyl parahydroxybenzoate | 0.02% |
| Lactic acid/sodium lactate | QS pH 3.5 to 4.5 |
| Demineralized water QS | 100% |

Example Number 4: Bio-Adhesive Gel for Oral Mycoses

| | |
|---|---|
| Lambda-carrageenans | 2.50% |
| Lecithin (Soya bean) | 7.5% |
| Glycerine | 12% |
| Miconazole | 2.00% |
| Pre-gelatinized starch | 2.50% |
| Polysorbate 20 | 2.00% |
| Sodium methyl parahydroxybenzoate | 0.08% |
| Sodium propyl parahydroxybenzoate | 0.02% |
| Demineralized water QS | 100% |

The invention claimed is:

1. Viscous liquid compositions for applications on oral mucous membrane, nasal mucous membrane, rectal mucous membrane covering the distal part of the large intestine, vaginal mucous membrane, or ocular mucous membrane, having a bio adhesive prolonged action or release and comprising:
   i) a polysaccharide matrix agent selected from the group constituting of lambda carrageenan or iota carrageenan, allowing the in situ formation of a matrix film with a reinforced bio-adhesive capacity due to complexation reactions between the polysaccharide matrix agent and the components of the local secretions of the mucous membranes,
   ii) at least one non-ionic surface acting agent comprising a mixture of phospholipid comprising phosphatidylcholine and phosphatidylserine as a reinforcing agent of the intrinsic bio-adhesive properties of the polysaccharide matrix agent,
   iii) a hydration medium for the polysaccharide matrix agent,
   iv) glycerol,
   v) an active ingredient.

2. Viscous liquid compositions having a bio adhesive prolonged action or release according to claim 1, wherein the carrageenan concentration is ranged between 0.5 and 30% in mass in the relation of the total mass of the composition.

3. Viscous liquid compositions having a bio adhesive prolonged action or release according to claim 1, wherein the hydration medium of the polysaccharide matrix agent is an aqueous or hydro-alcoholic solution.

4. Viscous liquid compositions having a bio adhesive prolonged action or release according to claim 3, wherein the hydro-alcoholic phase includes ethanol or isopropyl alcohol.

5. Viscous liquid compositions having a bio adhesive prolonged action or release according to claim 3, wherein the proportion of the alcoholic phase lies between 10% and 90% in mass in the relation of the total mass of the hydration medium.

6. Viscous liquid compositions having a bio adhesive prolonged action or release according to claim 1, wherein alkaline or alkaline earth ions are dissolved in the hydration medium to obtain a better hydration of the carrageenans in the medium.

7. Viscous liquid compositions having a bio adhesive prolonged action or release according to claim 6, wherein the concentration of alkaline and alkaline earth ions is in a range from 0.01% to 50% in mass in relation to the total mass of the composition.

8. Viscous liquid compositions having a bio adhesive prolonged action or release according to claim 6, wherein the alkaline and alkaline ions are added under hydroxide form or under hydrochloric, sulphuric, nitric, phosphoric, citric salt form.

9. Viscous liquid compositions having a bio adhesive prolonged action or release according to claim 1, wherein the aqueous phase of the hydration medium is a buffer solution.

10. Viscous liquid compositions having a bio adhesive prolonged action or release according to claim 9, wherein the pH value of the buffer solution is in a range from 5 to 12.

11. Viscous liquid compositions having a bio adhesive prolonged action or release according to claim 9, wherein the buffer solution is constituted by the couples of citric acid/citrate, citric acid/sodium hydroxide, lactic acid/lactate, monosodium phosphate/disodium phosphate, monopotassium phosphate/potassium phosphate, bicarbonate/carbonate, or boric acid/sodium borate.

12. Viscous liquid compositions having a bio adhesive prolonged action or release according to claim 1 further comprising a moistening agent, wherein the moistening agent is selected from the group consisting of glycerine, sorbitol, mannitol, xylitol and maltitol.

13. Viscous liquid compositions having a bio adhesive prolonged action or release according to claim 12, wherein concentration of moistening agent is in a range from 1% to 30% in mass in relation to the total mass of the liquid phase.

14. Viscous liquid compositions having a bio adhesive prolonged action or release according to claim 1 further comprising a strengthening structure, wherein the strengthening structure agent is selected from the group consisting of rice, potato, corn and manioc starches and their derivatives.

15. Viscous liquid compositions having a bio adhesive prolonged action or release according to claim 1 further comprising a starch, wherein the starch concentration is in a range from 0.01% to 50% in mass in relation to the total mass of the composition.

16. Viscous liquid compositions having a bio adhesive prolonged action or release according to claim 1 further comprising a preservative, wherein the preservative concentration is in a range from 0% to 10% in mass in relation to the total mass of the composition.

17. Viscous liquid compositions having a bio adhesive prolonged action or release according to claim 1 further comprising a dye, wherein the dye concentration is in a range from 0.01% to 5% in mass in relation to the total mass of the composition.

18. Viscous liquid compositions having a bio adhesive prolonged action or release according to claim 1 further comprising a sweetening agent, wherein the sweetening agent is selected from the group consisting of saccharose, aspartame, acesulfam, sodium cyclamate, and sodium saccharin.

19. Viscous liquid compositions having a bio adhesive prolonged action or release according to claim 18, wherein sweetening agent concentration is in a range from 0.01% to 30% in mass in relation to the total mass of the composition.

20. Viscous liquid compositions having a bio adhesive prolonged action or release according to claim 1, wherein the active ingredient belongs to a therapeutic class selected among analgesics, anti-inflammatories, antispasmodics, cytotoxics, antibiotics, anti-fungals, disinfectants, anti-parasitic, hormones, anti-virals, anti-migraine agents, anti-allergics, respiratory agents, analeptics, spermicides, anti-haemorrhoidal agents, vasoconstrictors, vasodilators, antipuritics, uterorelaxants, anti-glaucoma agents, mydriatics, and anti-asthmatics.

21. Viscous liquid compositions having a bio adhesive prolonged action or release according to claim 1, wherein the active ingredient is dispersed or solubilized in the hydration medium or in an organic solvent.

22. Viscous liquid compositions having a bio adhesive prolonged action or release according to claim 21, wherein the organic solvent is selected from the group consisting of vegetable oils, mineral oils, natural oils, synthetic oils, and other organic solvents.

23. Viscous liquid compositions having a bio adhesive prolonged action or release according to claim 21, wherein the granulometric distribution of the dispersed active ingredient is spread from 10 μm to 1000 μm.

24. Viscous liquid compositions having a bio adhesive prolonged action or release according to claim 21, wherein the granulometry of the dispersed active ingredient lies between 10 μm and 250 μm.

25. Viscous liquid compositions having a bio adhesive prolonged action or release according to claim 1, wherein their viscosity is ranged between 100 mPas and 500,000 mPas.

26. Viscous liquid compositions having a bio adhesive prolonged action or release according to claim 1, wherein application routes are oral mucous membrane, nasal, vaginal and rectal mucous membranes.

27. Viscous liquid compositions having a bio adhesive prolonged action or release according to claim 26, wherein the time release of the active ingredient is ranged between 2 and 12 hours for the oral, nasal and ocular routes.

28. Viscous liquid compositions having a bio adhesive prolonged action or release according to claim 26, wherein the time release of the active ingredient is greater than 12 hours for the vaginal route.

29. Viscous liquid compositions having a bio adhesive prolonged action or release according to claim wherein the solvent includes an alcohol selected from ethanol, propanol and butanol.

30. Viscous liquid compositions having a bio adhesive prolonged action or release according to claim 1 wherein the solvent includes a polyol selected from glycerol, propylene glycol, polyoxyethylene glycol.

31. Viscous liquid compositions for applications on oral mucous membrane, nasal mucous membrane, rectal mucous membrane covering the distal part of the large intestine, vaginal mucous membrane, or ocular mucous membrane, having a bio adhesive prolonged action or release and comprising:
   i) a polysaccharide matrix agent selected from the group constituting of lambda carrageenan or iota carrageenan, allowing the in situ formation of a matrix film with a reinforced bio-adhesive capacity due to complexation reactions between the polysaccharide matrix agent and the components of the local secretions of the mucous membranes;
   ii) at least one non-ionic surface acting agent comprising a mixture of phospholipid comprising phosphatidylcholine and phosphatidylserine;
   iii) a hydration medium for the polysaccharide matrix agent;
   iv) glycerol;
   v) an active ingredient,
   wherein the glycerol (iv) concentration relates to the at least one non-ionic surface acting agent (ii) concentration for a ratio minimum equal to 1:0.8.

32. Viscous liquid compositions having a bio adhesive prolonged action or release according to claim 31, wherein the at least one non-ionic surface acting agent concentration varies from 0.1% to 50% in weight in relation to the total mass of the excipients.

33. Viscous liquid compositions having a bio adhesive prolonged action or release according to claim 31, further including a solvent selected from ethanol, propanol and butanol.

34. Viscous liquid compositions having a bio adhesive prolonged action or release according to claim 31, further including a polyol selected from propylene glycol, and polyoxyethylene glycol.

35. Viscous liquid compositions having a bio adhesive prolonged action or release according to claim 31, wherein the active ingredient is dispersed or solubilized in the hydration medium or in an organic solvent.

36. Viscous liquid compositions having a bio adhesive prolonged action or release according to claim 31, wherein the active ingredient belongs to a therapeutic class selected among analgesics, anti-inflammatories, antispasmodics, cytotoxics, antibiotics, anti-fungals, disinfectants, anti-parasitic, hormones, anti-virals, anti-migraine agents, anti-allergics, respiratory agents, analeptics, spermicides, anti-haemorrhoidal agents, vasoconstrictors, vasodilators, antipurities, uterorelaxants, anti-glaucoma agents, mydriatics and anti-asthmatics.

37. Viscous compositions according to claim 31 wherein the glycerol (iv) concentration relates to the at least one non-ionic surface acting agent (ii) concentration for a ratio minimum equal to 1:1.6.

* * * * *